United States Patent [19]
Greenwood et al.

[11] Patent Number: 5,886,250
[45] Date of Patent: Mar. 23, 1999

[54] PITCH-CATCH ONLY ULTRASONIC FLUID DENSITOMETER

[75] Inventors: Margaret S. Greenwood, Richland; Robert V. Harris, Pasco, both of Wash.

[73] Assignee: Battelle Memorial Institute, Richland, Wash.

[21] Appl. No.: 928,204

[22] Filed: Sep. 12, 1997

Related U.S. Application Data

[63] Continuation-in-part of Ser. No. 628,834, Apr. 5, 1996, Pat. No. 5,708,191.

[51] Int. Cl.⁶ .................................................. G01N 9/00
[52] U.S. Cl. ........................................ 073/32 A; 73/54.41
[58] Field of Search ................... 73/32 A, 54.01, 73/54.41, 64.53, 61.75, 61.79, 597, 628, 644

[56] References Cited

U.S. PATENT DOCUMENTS

| | | | |
|---|---|---|---|
| 4,149,139 | 4/1979 | Kronk | 367/93 |
| 4,320,659 | 3/1982 | Lynnworth et al. | 73/589 |
| 4,571,693 | 2/1986 | Birchak et al. | 73/24.01 |
| 4,821,838 | 4/1989 | Chen | 181/175 |
| 4,893,496 | 1/1990 | Bau et al. | 73/32 A |
| 4,991,124 | 2/1991 | Kline | 73/32 A |
| 5,365,778 | 11/1994 | Sheen et al. | 73/54.41 |

OTHER PUBLICATIONS

Research and Development Magazine, Oct., 1994, p. 15.
Sheen, et al., "An In–Line Ultasonic Viscometer," Review of Progress in Quantitative Nondestructive Evaluation, vol. 14a pp. 1151–1158, 1995.

*Primary Examiner*—Hezron Williams
*Assistant Examiner*—Richard A. Moller
*Attorney, Agent, or Firm*—Paul W. Zimmerman

[57] ABSTRACT

The present invention is an ultrasonic fluid densitometer that uses a material wedge and pitch-catch only ultrasonic transducers for transmitting and receiving ultrasonic signals internally reflected within the material wedge. Density of a fluid is determined by immersing the wedge into the fluid and measuring reflection of ultrasound at the wedge-fluid interface.

10 Claims, 3 Drawing Sheets

PITCH-CATCH ONLY ULTRASONIC FLUID DENSITOMETER

This patent application is a Continuation-In-Part of patent application Ser. No. 08/628,834 filed Apr. 5, 1996, now U.S. Pat. No. 5,708,191.

This invention was made with Government support under Contract DE-AC06-76RLO 1830 awarded by the U.S. Department of Energy. The Government has certain rights in the invention.

FIELD OF THE INVENTION

The present invention is an apparatus and method for measuring fluid density. More specifically, the invention relies upon acoustic impedance matching of a wedge material and a fluid wherein the wedge material is immersed into the fluid for determination of the density of the fluid.

BACKGROUND OF THE INVENTION

Use of sound waves, specifically ultrasonic sound waves for determining fluid density is well known. An ultrasonic sensor for measuring fluid density was reported by S. Sheen at Argonne National Laboratory. It received a R&D 100 Award in 1994 and a description appeared in the Research and Development magazine in October, 1994, p. 15.

Sheen describes an ultrasonic densitometer (FIG. 1) for measuring a density of a fluid 100. The ultrasonic densitometer has a wedge material 102 wherein the wedge material 102 has at least two side substantially parallel. A first parallel side 104 has a first ultrasonic transducer 106 mounted thereon and a second parallel side 108 immersible into said fluid whereby a first portion of an ultrasonic signal emanating from said first ultrasonic transducer 106 strikes the second parallel side 108 and reflects back to the first parallel side 104 providing a reflection coefficient. A second portion of the ultrasonic signal propagates through the fluid 100, strikes a second wedge immersed surface 110 and reflects back to the first ultrasonic transducer 106 providing a speed of sound in the fluid. The arm surfaces 112 of the T in contact with air for reference measurements. The T-shaped wedges 102 are mounted through the wall of a pipe 114 so that the fluid 100 within the pipe passes between the immersed surfaces 108, 110 of the two T-shaped wedges 102, 102a. From the reflection coefficient and the speed of sound in the fluid, the density of the fluid is obtained. In a second paper S. H. Sheen, H. T. Chien, and A. C. Raptis, "An In-Line Ultrasonic Viscometer," Review of Progress in Quantitative Nondestructive Evaluation, Vol. 14a, pp 1151–1158, 1995, Sheen specifies that the T-shaped wedge material is aluminum. The second transducer generates shear waves used for determining viscosity. A disadvantage of Sheen's ultrasonic densitometer is that because the wedge material is aluminum, the acoustic impedance of the wedge material is much greater than the acoustic impedance of the fluid so that a substantial change in density (eg. 10%) results in a quite small change in the aluminum/liquid reflection coefficient of about 0.014. Secondarily, the ultrasonic signal is required to reflect through the fluid of interest thereby requiring the requisite target surface of a second T-shaped wedge. Further, for fluids attenuative of ultrasound, density measurements would not be obtainable.

Another ultrasonic fluid meter is described in M. S. Greenwood, J. L. Mai, and M. S. Good, "Attenuation measurement of ultrasound in a kaolin-water slurry: A linear dependence upon frequency," J. Acoust. Soc. Am. 94, 908–916 (1993).

This ultrasonic attenuation sensor was developed for concentration measurements in a $\frac{1}{12}$-scale model of a double-shell tank. Because fluid density is a function of concentration, this unit may be used to determined fluid density as well as fluid concentration. The sensor consists of a send transducer and a receive transducer, separated by 4 inches. The ultrasound produced by the send transducer travels through a liquid (or slurry) where it is attenuated. The signal recorded by the receive transducer indicates how much attenuation has occurred. However, the instrument required calibration by making measurements in the laboratory for that specific slurry formulation so that concentration of the slurry could be correlated with voltage of signal in receive transducer. Again, this ultrasonic densitometer required that the ultrasonic signal be detected after passing through the fluid, in this case slurry, of interest and further required prior laboratory calibration.

Commercially available ultrasonic fluid concentration measuring devices are available through JM Science Inc, Buffalo, N.Y., Manufactured by: Fuji Ultrasonic Engineering Co., Ltd. In operation, an ultrasonic transducer produces ultrasound that propagates through the fluid of interest then is reflected by a metal plate about an inch away from the transducer. The reflected signal returns to the transducer and the time for a round trip is determined. Since the distance is known, the velocity of ultrasound in the liquid can be determined. The Fuji sensor correlates the speed of sound with a concentration of a particular fluid solution and with temperature of the particular fluid solution and requires laboratory calibration. As with Greenwood et al., the reflected ultrasonic signal must pass through the fluid of interest and the instrument requires calibration.

There is a need in the field of ultrasonic densitometry for an ultrasonic fluid densitometer that has greater sensitivity, does not require calibration and does not require a reflected signal to pass through the fluid of interest.

SUMMARY OF THE INVENTION

The present invention is a pitch-catch only ultrasonic densitometer for measuring a density of a fluid. The pitch-catch only ultrasonic densitometer has a wedge material with at least two non-parallel sides, a first non-parallel side having a first ultrasonic transducer mounted thereon and a second non-parallel side immersible into the fluid whereby an ultrasonic signal emanating from the first ultrasonic transducer strikes the second non-parallel side and reflects therefrom. The improvement of the present invention is that the wedge material further has a third non-parallel side with a first receiving transducer for receiving the signal emanated from the first ultrasonic transducer and reflected from the second non-parallel side; and a second ultrasonic transducer mounted on a fourth non-parallel side for emanating a signal to the second non-parallel side and reflecting to a fifth non-parallel side having a second receiving transducer thereon.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT (S)

Figure 1:
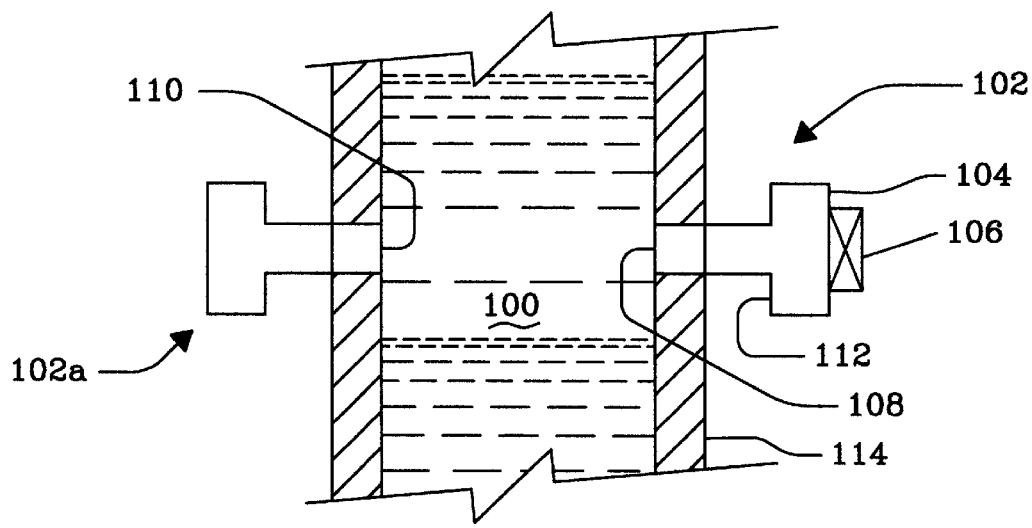
FIG. 1 is a cross section of a prior art ultrasonic densitometer.

According to the present invention, it is preferred that the fluid 100 and the wedge material 102 have a ratio of an acoustic impedance of the wedge material to an acoustic impedance of the fluid that is less than 11. Table 1 shows acoustic impedances for candidate wedge materials and ratio of acoustic impedance of those materials to the acoustic impedance of water which has an acoustic impedance of 1.5 ($10^6$) kg/m²s. By using a wedge material 102 having an acoustic impedance ratio to the fluid of less than 11, there is an increased change in reflection coefficient which increases the sensitivity of the ultrasonic densitometer. Specifically for Rexolite (C-LEC Plastics, Inc. Beverly, N.J.), for a 10% change in fluid density, there is a change of about 0.05 of the reflection coefficient.

TABLE 1

Acoustic Impedances

| Material | Acoustic Impedance (kg/m²s) | Ratio to Water |
|---|---|---|
| Aluminum | 17 ($10^6$) | 11.33 |
| Lead | 25 ($10^6$) | 16.67 |
| Steel | 45 ($10^6$) | 30.00 |
| Rexolite | 2.5 ($10^6$) | 1.67 |

It is preferred that the acoustic impedance ratio be less than about 5 and more preferably less than about 3 when the fluid is a liquid. Plastic includes polymers including but not limited to Rexolite, Loten (Sigma Transducers, Kennewick, Wash.), and acrylics.

Fluids that can be measured are preferably liquid. A liquid may be a liquid solution, or mixture having solid particles or immiscible phases. Immiscible phases include liquids and gases. In mixtures, it is preferred that the non-soluble phase be of a size smaller than a wavelength of the ultrasonic waves. It is further preferable that the mixture be homogenous and may require mixing. When a gas (eg air) phase is present, it is preferred to use a minimum measurement in a series of measurements to obtain the most accurate measure of density. The reason is that gas bubbles may adhere to the surface of the immersed wedge material and increase the reflectance of ultrasound at the wedge material-gas interface.

A further advantage is realized when all detected ultrasonic signals are detected on the basis of ultrasonic reflections internal to the wedge material. More specifically, the present invention extends beyond the embodiment shown in FIG. 2 and variations thereof. The wedge material 102 has at least two side substantially parallel. A first parallel side 104 has an orthogonal ultrasonic transducer 106 mounted thereon and a second side 108 immersible into said fluid whereby a first portion of an ultrasonic signal emanating from said first ultrasonic transducer 106 strikes the second side 108 and reflects back to the first parallel side 104. The wedge material 102 further has (a) a first non-parallel side 200 with a first ultrasonic transducer 206 from which emanates an ultrasonic signal toward a third non-parallel side 202; and (b) a receiving ultrasonic transducer 204 mounted on the third non-parallel side 202 for receiving the reflected ultrasonic signal from the first ultrasonic transducer 206.

Figure 2:
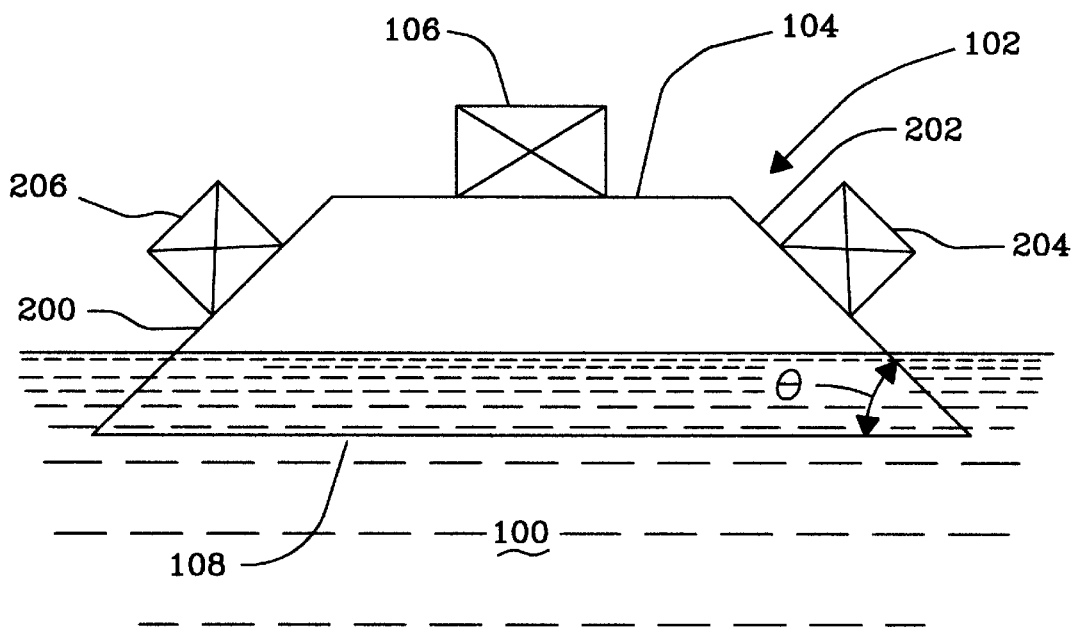
FIG. 2 is a three transducer embodiment of pulse-echo with pitch-catch.

In FIG. 2, each of the first and third non-parallel sides 200,202 is connected to the first and second parallel sides 104, 108. A transmitting transducer 206 is mounted on the first non-parallel side 200 whereby the transmitting transducer transmits said second ultrasonic signal that reflects from said second parallel side 108 creating the second reflected ultrasonic signal that is received by the receiving transducer 204.

Figure 3:
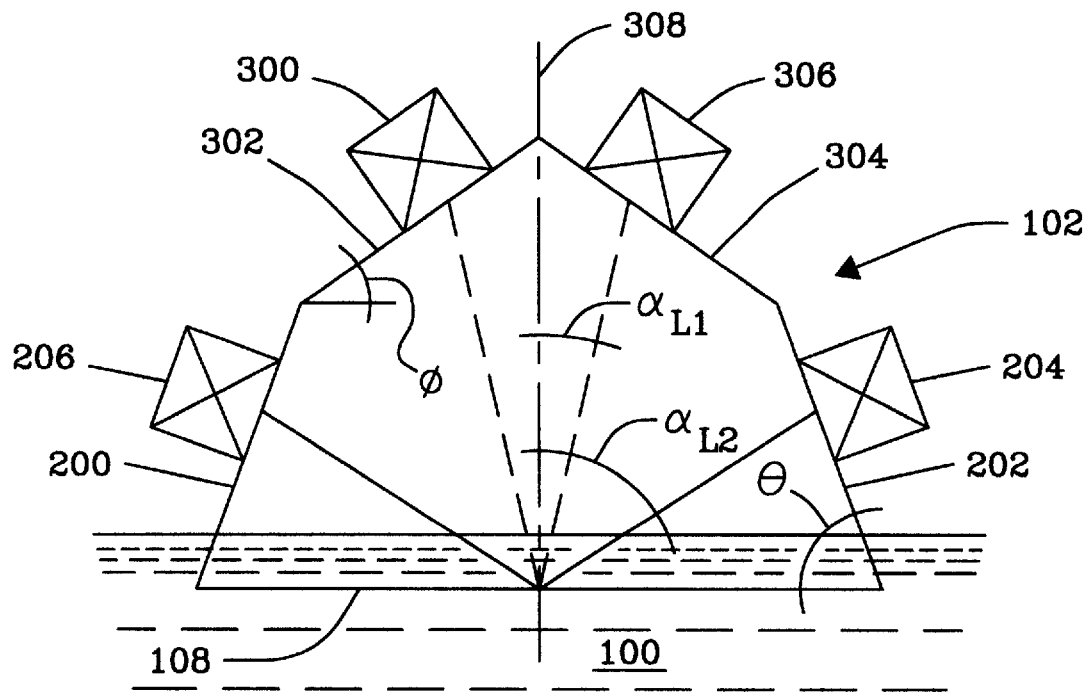
FIG. 3 is a four transducer embodiment of the present invention, pitch-catch only.
Figure 5:
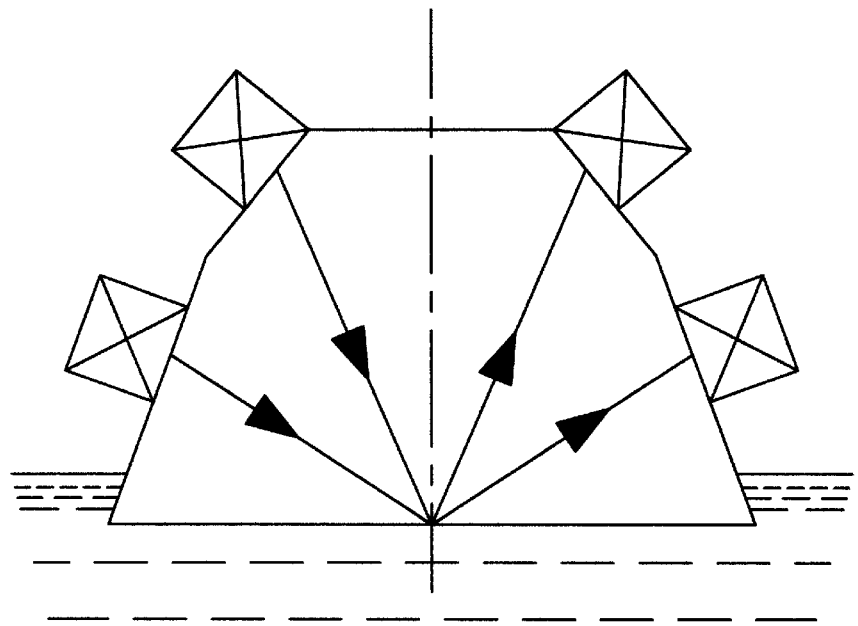
FIG. 5 shows an alternative wedge material shape.
Figure 6:
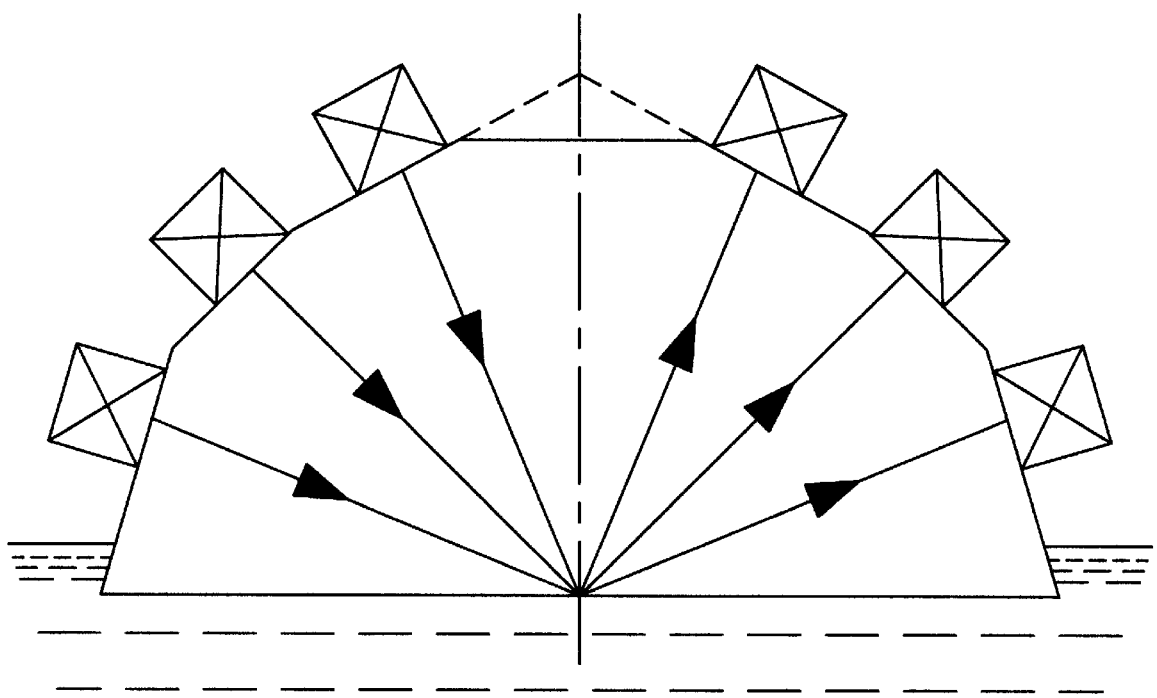
FIG. 6 shows further wedge material shape and transducer deployment.

In a further embodiment, it is beneficial to omit the pulse-echo transducer 106 on the first parallel side 104 and have two pairs of transducers as shown in FIG. 3. In this pitch-catch only embodiment, the ultrasonic densitometer for measuring a density of a fluid 100 has a wedge material 102 with at least two non-parallel sides a first non-parallel side 200 having a first ultrasonic transducer 206 mounted thereon and a second non-parallel side 108 immersible into said fluid whereby an ultrasonic signal emanating from said first ultrasonic transducer 206 strikes the second non-parallel side 108 and reflects therefrom. The improvement further has a third non-parallel side 202 with a first receiving transducer 204 for receiving a signal emanated from the first ultrasonic transducer 206 and reflected from the second non-parallel side 108; and a second ultrasonic transducer 300 mounted on a fourth non-parallel side 302 for emanating a signal to the second non-parallel side 108 and reflecting to a fifth non-parallel side 304 having a second receiving transducer 306 thereon. The wedge material 102 is not limited to the shape in FIG. 3 as illustrated in FIG. 5. Additional sides and transducers may be used, especially for measurements in viscous fluids as shown in FIG. 6.

The wedge material 102 may be further characterized by consideration of the second non-parallel side 108 in combination with a normal 308 to the second non-parallel side 108. The first non-parallel side 200 makes a first angle with the second non-parallel side 108 that is the same as the first angle $\alpha_{L2}$ between the signal emanated from the first ultrasonic transducer 206 and the normal 308. The fourth non-parallel side 302 makes a second angle with the second non-parallel side 108 that is the same as the second angle $\alpha_{L1}$ between the signal emanated from the second ultrasonic transducer 300 and the normal 308. In a preferred embodiment, the second angle $\alpha_{L1}$ (phi) is less than the first angle $\alpha_{L2}$ (theta). It is further preferred that the second angle $\alpha_{L1}$ is less than about 45 degrees, more preferably less than about 20 degrees, yet more preferably less than about 10 degrees and most preferably about 5 degrees. It is preferred that the first angle $\alpha_{L2}$ is greater than about 45 degrees, preferably about 60 degrees. The greater the difference between $\alpha_{L1}$ and $\alpha_{L2}$, the more accurate the density determination.

While the combined pulse-echo/pitch-catch apparatus and method shown in FIG. 2 is mathematically simple because the pulse-echo angle is zero, the pulse-echo signal has greater noise and the electronics must handle both pulse-echo and pitch-catch. Accordingly, use of pitch-catch only would reduce the noise and complexity of the apparatus and method. An analytic solution of the mathematical equations using any two angles has been found. According to the present invention, it is preferred that both angles be non zero (pitch-catch only).

Figure 4:
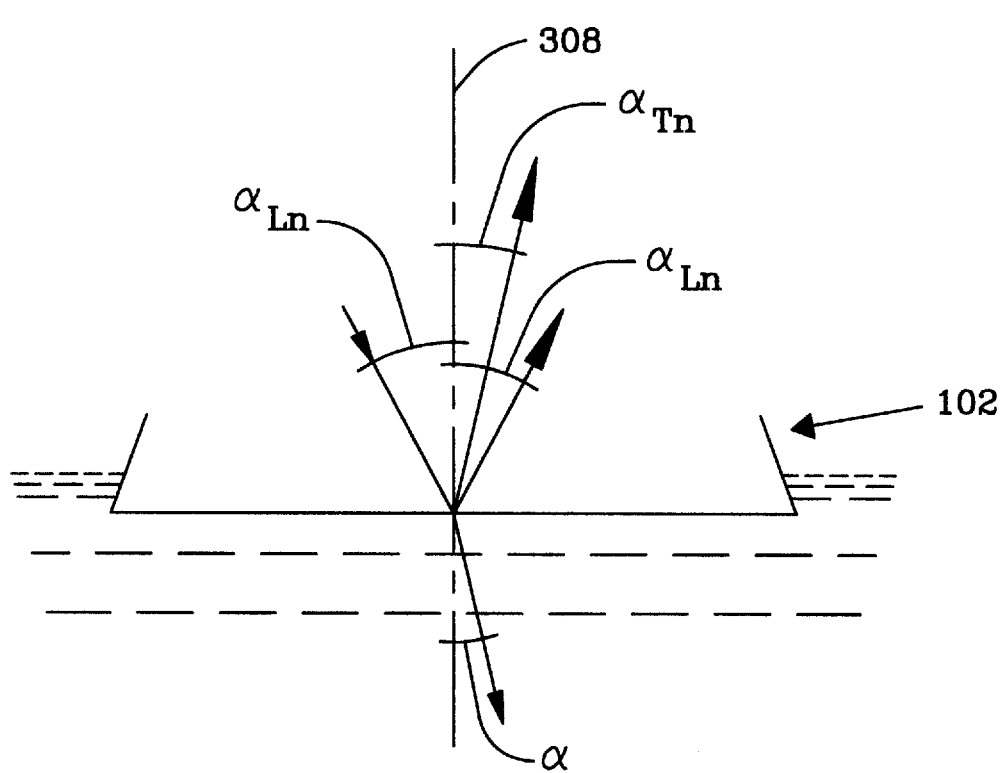
FIG. 4 is a diagram defining angles of ultrasound propagation according to Snell's law of refraction.

In the case where the pulse-echo transducer 106 is omitted, the density is computed from $$\rho^2 = \frac{(\sin\alpha_{L2})^2 - (\sin\alpha_{L1})^2}{(\cos\alpha_{L1}/\rho_w J_1)^2 - (\cos\alpha_{L2}/\rho_w^2 J_2)^2}$$

where $$J_n = -G_n + H_n(1 + RLLX_n)/(1 - RLLX_n)$$

wherein $RLLX_n$ (n=1,2) are the measured reflection coefficients for the transducers emitting signals at angles $\alpha_{L1}$ and $\alpha_{L2}$ respectively. Parameters $G_n$ and $H_n$ depend upon the angles and speed of sound in the wedge material.

$$G_n = (c_t/c_L)^2 \sin 2\alpha_{Ln} \sin 2\alpha_{Tn}$$
$$H_n = \cos^2 2\alpha_{Tn}$$

where $c_t$ is the speed of the shear wave and $c_L$ is the speed of the longitudinal wave in the wedge material 102 and the angles are as shown in FIG. 4 conforming to Snell's law of refraction. Shear angle $\alpha_{Tn}$ is obtained from $$\sin \alpha_{Tn} = (c_t/c_L) \sin \alpha_{Ln}$$

For the embodiment shown in FIG. 2, it is necessary to know a-priori the speed of sound in the wedge material 100.

The angle theta of the non-parallel sides 200, 202 to the second parallel side 108 is critical to the present invention for sensitivity to small changes in fluid density. ,An angle of 20 degrees provided limited sensitivity whereas an angle of about 60 degrees provided greater sensitivity to changes in fluid density. Accordingly, the angle theta is preferable greater than about 20 degrees and more preferable greater than about 30 degrees.

In the embodiment of FIG. 3, The fourth and fifth non-parallel sides 302, 304 make a second angle phi with said first parallel side different from the first angle theta. These additional sides and transducers may be used to determine the sign of the reflection coefficients. Alternatively, analysis of signal phase may be done to determine the sign of the reflection coefficient without using the second transmitting and receiving transducers 300, 306. However, additional electronic circuitry and possibly additional software for data reduction would be needed for analysis of signal phase, which is less preferred. In the embodiment of FIG. 6, two of the pitch-catch sets may be used to determine fluid density and the third set used to determine the sign of the reflection coefficient.

The transducers may be any ultrasonic transducers, preferably emitting in a range from about 0.5 MHZ to about 10 MHZ.

Electrical signals from the transducers may be collected for analysis in at least two ways. In one way, A function generator (not shown) may be applied to the transmitting transducer 206. The ultrasound reflected at the second parallel side 108 of the wedge material 102 produces a response in the receive transducer 204. This RF-signal, after amplification by a receiver (not shown) is sent to a 12-bit digitizer to obtain a signal that can be analyzed by a computer. A 12-bit digitizer can detect very small changes in voltage. The maximum value of the signal will be determined using software. A multiplexer system will sequentially send the toneburst signal to each send transducer and obtain the return signal. An algorithm will be developed to take averages and, in the case of the slurry, to look for minimum values in the signal and to process this data to produce an on-line value of the density and velocity of sound.

The pitch-catch only densitometer of the present invention is further useful in determination of density of a viscous fluid. To the extent that a fluid can support a shear wave, the amount of energy of the shear wave that is transmitted into the fluid reduces the amount of energy in all other reflected ultrasonic waves (e.g. longitudinal and/or shear wave in the wedge material). For low viscosity fluids, the amount of energy in a transmitted shear wave in the fluid is negligible, whereas for medium to high viscosity fluids, it is small but not negligible. By observing the strength of the reflected longitudinal wave, one may determine whether the fluid is detectably viscous. More specifically, by using at least 3 pair of pitch-catch transmitter/receiver sets as shown in FIG. 6, sufficient data are gathered to support solving three equations for three unknowns of (1) density of liquid, (2) longitudinal speed in liquid, and (3) shear speed in liquid. When a fluid is sufficiently viscous, a 2-pair set (FIG. 5) only provides sufficient information to solve for two unknowns, (1) density of the fluid and (2) longitudinal speed in fluid, and would inaccurately predict density of the liquid.

EXAMPLE 1

An experiment was conducted to demonstrate the ultrasonic densitometer of the present invention. The fluid 100 was a sugar water solution with a density of 1.07 g/cm$^3$. The wedge material 102 is Rexolite. The wedge material 102 shape was as in FIG. 3 with 5 sides. Angles theta and phi were 60 and 42 degrees respectively. The density as determined ultrasonically was 1.05 g/cm$^3$, which was within about 2% of the actual density. By increasing the difference between the angles, for example using a 5 degree angle in place of the 42 degree angle, the measured density would be nearer the actual density.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A pitch-catch only ultrasonic densitometer for measuring a density of a fluid, said ultrasonic densitometer having a wedge material, said wedge material having at least two non-parallel sides, a first non-parallel side having a first ultrasonic transducer mounted thereon and a second non-parallel side immersible into said fluid whereby an ultrasonic signal emanating from said first ultrasonic transducer strikes said second non-parallel side and reflects therefrom; the improvement comprising:

said wedge material further having a third non-parallel side with a first receiving transducer mounted thereon for receiving a signal emanated from the first ultrasonic transducer and reflected from the second non-parallel side; and said wedge material further having fourth non-parallel side with a second ultrasonic transducer mounted thereon for emanating a signal to the second non-parallel side and reflecting to a fifth non-parallel side of said wedge material having a second receiving transducer mounted thereon; providing the pitch-catch only densitometer.

2. The pitch-catch only ultrasonic densitometer as recited in claim 1, wherein said signal emanating from said first ultrasonic transducer mounted on said first non-parallel side makes a first angle with a normal of said second non-parallel side of greater than about 45 degrees.

3. The pitch-catch only ultrasonic densitometer as recited in claim 2, wherein said first angle is about 60 degrees.

4. The pitch-catch only ultrasonic densitometer as recited in claim 1, wherein said signal emanating from said second ultrasonic transducer makes a second angle with a normal of said second non-parallel side of less than about 45 degrees.

5. The pitch-catch only ultrasonic densitometer as recited in claim 4, wherein said second angle is less than about 20 degrees.

6. The pitch-catch only ultrasonic densitometer as recited in claim 5, wherein said second angle is less than about 10 degrees.

7. The pitch-catch only ultrasonic densitometer as recited in claim 6, wherein said second angle is about 5 degrees.

8. The pitch-catch only ultrasonic densitometer as recited in claim 1, further comprising additional non-parallel sides and additional transducers thereon up to a total of at least six transducers.

9. A method of measuring density of a fluid, comprising the steps of:

forming a wedge material having at least two non-parallel sides, a first non-parallel side having a first ultrasonic transducer mounted thereon and a second non-parallel side immersible into said fluid whereby an ultrasonic signal emanating from said first ultrasonic transducer strikes said second non-parallel side and reflects therefrom; the improvement comprising:

forming a third non-parallel side on the wedge material and mounting a first receiving transducer thereon for receiving a signal emanated from the first ultrasonic transducer and reflected from the second non-parallel side;

mounting a second ultrasonic transducer on a fourth non-parallel side formed on the wedge material for emanating a signal to the second non-parallel side and reflecting to a fifth non-parallel side formed on the wedge material having a second receiving transducer thereon; and immersing said second non-parallel side into the fluid and measuring the density of the fluid.

10. The method as recited in claim 9, wherein said fluid is viscous, further comprising the steps of:

forming a third set of non-parallel sides and mounting a third set of transducers thereon and obtaining sufficient data to determine a density of the viscous fluid.

* * * * *